United States Patent [19]

Chambers

[11] Patent Number: 4,625,719
[45] Date of Patent: Dec. 2, 1986

[54] ADJUSTABLE ARM SLING

[76] Inventor: David H. Chambers, 2890 Griffin Rd., Ste. #4, Fort Lauderdale, Fla. 33004

[21] Appl. No.: 755,700

[22] Filed: Jul. 16, 1985

[51] Int. Cl.[4] .............................................. A61F 5/40
[52] U.S. Cl. .............................. 128/94; 128/DIG. 15
[58] Field of Search ............. 128/94, 77, 84, DIG. 15

[56] References Cited

U.S. PATENT DOCUMENTS

| | | | |
|---|---|---|---|
| 980,464 | 1/1911 | Wermuth | 128/94 |
| 1,304,153 | 5/1919 | Bugge | 128/94 |
| 2,644,448 | 7/1953 | Jardine | 128/94 |
| 2,875,754 | 3/1959 | Messer | 128/94 |
| 3,103,216 | 9/1963 | Scott | 128/94 |
| 4,232,664 | 11/1980 | Blatt | 128/94 |

FOREIGN PATENT DOCUMENTS 89148 3/1957 Norway ................... 128/94

Primary Examiner—Robert P. Swiatek
Assistant Examiner—John G. Weiss
Attorney, Agent, or Firm—Seed and Berry

[57] ABSTRACT

An adjustable arm sling has a flexible body with two sets of supporting loops of adjustable length therearound providing tags which adjustably connect with crossed shoulder straps anchored near the ends of the sling body. Hook and loop type fastener strips are preferably used for the loop adjustments and for the adjustable connection of the shoulder straps to the tags.

10 Claims, 2 Drawing Figures

ADJUSTABLE ARM SLING

TECHNICAL FIELD

The present invention relates to adjustable arm slings of the type in which a flexible sling body is supported by shoulder straps.

Various strap and buckle arrangements have been provided in the past for supporting arm slings and allowing adjustment to the support level of the sling body. However, in large part the adjustments have not been easy to initially make or vary, particuclrly when only slight variations were desired, and the desired comfort factor has not been easy to achieve, if ever. Also, the desired ease of application as well as adjustment has been a shortcoming. A typical prior art arm sling is disclosed in U.S. Pat. Nos. 1,304,153 and 3,815,588.

Accordingly, the present invention aims to provide a comfortable arm sling that can be easily applied and adjusted, is inexpensive to produce, and is durable and washable.

DISCLOSURE OF INVENTION

In carrying out the present invention hook and loop type fasteners are used to permit a wide range of adjustaments of the sling body beneath and around the arm and from the shoulder support straps. The sling body is fabric and has a channel section closed at an elbow portion and open at the other end. Two pairs of adjustable strap components pass around the sling body and provide two tags which are adjustably connected to crossing shoulder straps anchored at opposite ends of the sling body.

BEST MODE FOR CARRYING OUT THE INVENTION

Figures 1, 2:
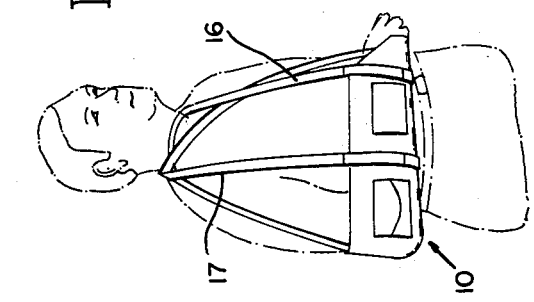
FIG. 1 is a perspective view showing an arm sling made in accordance with the present invention applied to a patient shown in phantom.
FIG. 2 is an isometric view of the arm sling with the shoulder straps centrally broken away and the sling body partly broken away, and with the fastener components matched by phantom lines.

Referring to the drawings it is seen that the adjustable arm sling of the present invention has a flexible sling body 10 made from a piece of a suitable fabric which is cut to a pattern, folded to double thickness, stitched, and turned inside out to provide finished seams. The pattern is such that the resulting sling body has a channel section and an elbow portion 10a having an elbow seam 11. The channel section has opposed front and back portions 10b-10c merging with a curved bottom portion 10c and together with the latter they merge with the elbow portion 10a. Opposite the elbow portion the sling body 10 is open and has downwardly sloped edges 10d and 10e front and back.

As part of the support for the sling body 10 there is provided a pair of straps 12-13, the first being located centrally of the sling body and the other near the sloped edges 10d-10e, respectively. These straps 12-13 will be designated hereinafter as the underarm strap and underwrist strap, respectively. Both are stitched longitudinally to the sling body fabric by stitching adjacent their side edges and extend upward beyond the back portion 10c, thereby forming tags 12a, 13a.

A second pair of straps 14-15 preferably overlies the front of the tags and is suitably secured thereto by longitudinal stitching and cross-stitching. These straps 14-15 will be designated hereinafter as the overarm strap and overwrist strap, respectively. Also provided are two shoulder straps 16-17. The first of these two straps is anchored to the sling body 10 at the top of the elbow portion 10a by suitable stitching and preferably has the illustrated slope at its anchored end portion. The other shoulder strap 17 is secured to the front portion 10b of the sling body near the top of the front sloped edge 10d by stitching and initially extends generally at right angles thereto as shown.

For securing the various straps together in the desired pattern there are provided four sets 20a-20b, 21a-21b, 22a-22b, and 23a-23b, of adjustable fastening components, preferably of the hook and loop type commonly referred to as Velcro type fasteners. Fastener components 20a and 21a are mounted on the front end portion of the underarm and underwrist straps 12, 13 and the complementing fastener components 20b, 21b are secured on the underside of the forward free end portion of the overarm and overwrist straps 14, 15. The third set of fasteners has component 23a mounted on the free end portion of shoulder strap 16 and component 22b at the front of tag 13a. Similarly, the fourth set of fasteners has one component 23a mounted on the free end portion of shoulder strap 17 and the other component 23b at the front of the tag 12a. More specifically, in the preferred embodiment the fastener components 22b, 23b are mounted on the portions of the overwrist and overarm straps 15, 14 which overlie the tags 13a, 12a, respectively. However, it will be recognized that the straps 14, 15 could be secured to the tags 12a, 13a only by cross-stitching and need not overlap the tags in the area to be occupied by the fastener components 22b, 23b, in which case these components can be secured directly to the tags.

The fastener components are preferably secured in place by stitching applied to the straps before the straps are stitched to the sling body 10. Also, it is preferred to stitch the straps 14, 15 to the tags 12a, 13a before the straps 12, 13 are stitched to the sling body 10.

Open and closed pockets 24, 25 may be provided for convenience at the front of the sling body 10, or at the back if they are desired to be hidden from view for security reasons.

The connecting pattern of the straps is indicated by broken lines in FIG. 2 and the general mounting position of the sling is shown in FIG. 1. In applying the sling to a patient the sling body 10 is placed under the arm with the elbow portion 10a at the elbow of the arm and the hand extending from the open end of the sling body. The sling body can then be secured to the patient's arm by pulling the overarm and overwrist straps 14, 15 forwardly over the forearm and approximately the wrist area and securing them to the underarm and underwrist straps 12, 13 to the desired sling snugness by way of the fastener sets 20a-20b and 21a-21b. The shoulder straps 16, 17 are then crossed at the patient's back and brought over the shoulders to mke connection with the tags 13a, 12a by way of the fastener sets 22a-22b and 23a-23b, respectively.

The effective length of the shoulder straps 16, 17 and the effective combined length of the pairs 12, 14 and 13, 15 of the other straps can be easily varied for comfort because of the length of the fastener component strips. The various straps can be made of any suitable material, but nylon webbing is preferred.

It will be noted that when the sling is in operative position the central and wrist supporting areas of the sling body 10 have direct support from the strap sets 12, 14 and 13, 15 when the tags 12a and 13a are connected to the respective shouldern straps 17, 16. This is an advantage over having the shoulder straps pulling at both of their ends directly on the fabric of the sling body 10.

It will be appreciated that, although specific embodiments of the invention have been described herein for purposes of illustration, various modifications may be made without departing from the spirit and scope of the invention. Accordingly, the invention is not limited except by the appended claims.

I claim:

1. An adjustable arm sling comprising:
   a flexible sling body formed to provide a channel section closed at one end by an elbow portion and open at the other end, said channel section having opposed front and back portions merging with a bottom portion and together with the bottom portion merging with the elbow portion;
   an underarm strap centrally of the sling body and an underwrist strap adjacent the open end of the sling body, said underarm and underwrist straps each passing beneath the sling body, being secured to the channel section, and having a respective tag at the top of the back portion of the channel section;
   an overarm strap and an overwrist strap fixed at a rear end to the tag of the underarm strap and the tag of the underwrist strap, respectively, and arranged to overlap at the front portion of the underarm strap and the underwrist strap, respectively;
   a first shoulder strap fixed to said elbow portion and having a free end portion arranged to overlap the tag of the underwrist strap;
   a second shoulder strap fixed to said channel section near the open end thereof and having a free end portion arranged to overlap the tag of the underarm strap; and
   four mating sets of hook and loop type fastening strips mounted at (a) the underside of the overarm strap and the front side of the underarm strap, (b) the underside of the underwrist strap and the front side of the underwrist strap, (c) said free end portion of the first shoulder strap and the tag of the underwrist strap, and (d) said free end portion of the second shoulder strap and the tag of the underarm strap.

2. An arm sling according to claim 1 in which said overarm strap has a rear portion overlapping the tag of the underarm strap and has the component of the set of hook and loop fasteners which is mounted at such tag secured to such overlapping rear portion of the overarm strap.

3. An arm sling according to claim 1 in which said overwrist strap has a rear portion overlapping the tag of the underwrist strap and has the component of the set of hook and loop fasteners which is mounted at such tag secured to such overlapping rear portion of the overwrist strap.

4. An arm sling according to claim 1 in which said overarm strap has a rear portion overlapping the tag of the underarm strap and has the component of the set of hook and loop fasteners mounted at such tag secured to such overlapping rear portion of the overarm strap, and in which said overwrist strap has a rear portion overlapping the tag of the underwrist strap and has the component of the set of hook and loop fasteners which is mounted at such tag secured to such overlapping rear portion of the overwrist strap.

5. An arm sling according to claim 1 in which said first shoulder strap is secured at the top and center of the elbow portion.

6. An arm sling according to claim 1 in which said front and back portions of the channel section slope downwardly adjacent the underwrist strap to the bottom portion of the channel section along their edges at the open end of the channel section.

7. An arm sling according to claim 6 in which said second shoulder strap is secured to the back portion of the channel section adjacent the juncture of the sloped edge of the back portion and edge of the bottom portion at the open end of the channel section.

8. An arm sling according to claim 1 in which said second shoulder strap is secured to the back portion of the channel section adjacent the open end thereof.

9. An arm sling according to claim 8 in which said first shoulder strap is secured adjacent the top and center of the elbow portion.

10. An arm sling according to claim 1 in which said underarm and underwrist straps are alike, and said overarm and overwrist straps are alike.

* * * * *